(12) United States Patent
Caldwell et al.

(10) Patent No.: US 7,645,721 B2
(45) Date of Patent: Jan. 12, 2010

(54) END GROUP ACTIVATED POLYMERS WITH OLIGONUCLEOTIDE LIGANDS

(75) Inventors: Karin D. Caldwell, Djursholm (SE); Jennifer A. Neff, Rancho Santa Margarita, CA (US)

(73) Assignee: Richard Nagler, Manhattan Beach, CA (US)

( * ) Notice: Subject to any disclaimer, the term of this patent is extended or adjusted under 35 U.S.C. 154(b) by 546 days.

(21) Appl. No.: 10/470,296

(22) PCT Filed: Feb. 4, 2002

(86) PCT No.: PCT/US02/03341

§ 371 (c)(1), (2), (4) Date: Jul. 28, 2003

(87) PCT Pub. No.: WO02/077159

PCT Pub. Date: Oct. 3, 2002

(65) Prior Publication Data
US 2004/0219541 A1    Nov. 4, 2004

Related U.S. Application Data

(60) Provisional application No. 60/266,081, filed on Feb. 2, 2001.

(51) Int. Cl.
*C40B 50/18*    (2006.01)

(52) U.S. Cl. .............................. 506/32; 506/37; 506/43; 435/6

(58) Field of Classification Search ...................... None
See application file for complete search history.

(56) References Cited

U.S. PATENT DOCUMENTS

| 5,470,705 | A |  | 11/1995 | Grossman et al. |
| 5,516,703 | A |  | 5/1996 | Caldwell et al. |
| 5,728,588 | A |  | 3/1998 | Caldwell et al. |
| 5,989,871 | A |  | 11/1999 | Grossman et al. |
| 6,060,246 | A | * | 5/2000 | Summerton et al. ............ 435/6 |
| 6,087,452 | A |  | 7/2000 | Stewart et al. |
| 6,284,503 | B1 |  | 9/2001 | Caldwell et al. |

OTHER PUBLICATIONS

Li et al. Chemical modification of surface active poly(ethyleneoxide)-poly(propylene oxide) triblock copolymers. 1996 Bioconjugate Chemistry 7:592-599.*

(Continued)

*Primary Examiner*—Christopher Low
*Assistant Examiner*—Christopher M. Gross
(74) *Attorney, Agent, or Firm*—Kirton & McConkie; Evan R. Witt (57) ABSTRACT

A method for coimmobilizing two or more biomolecules on a substrate in a defined ratio is disclosed. The method uses a copolymer conjugated to a number, N, of different types of oligonucleotides. The copolymer can be adsorbed to the surface of the substrate. N types of oligonucleotides complementary to the copolymer-bound oligonucleotides can be conjugated to N types of biomolecules. The types of the copolymer-bound oligonucleotides can be mixed in a defined ratio then adsorbed to the surface. The biomolecule-bound complementary oligonucletides can be conjugated to the copolymer-oligonucleotides to create a substrate with the biomolecules coimmobilized in a defined ratio. The invention also relates to a substrate prepared by the method of the invention.

35 Claims, 3 Drawing Sheets

OTHER PUBLICATIONS

Niemeyer et al. DNA-directed immobilization: efficient, reversible and site-selective surface binding of proteins by means of covalent DNA-streptaavidin conjugates. 1999 Analytical Biochemistry 268:54-63.*

Niemeyer et al. Functionalization of covalent DNA-streptavidin conjugates by means of biotinylated modulator components. 1999 Bioconjugate Chemistry 10:708-719.*

Niemeyer et al. Hybridization characteristics of biomolecular adapters, covalent DNA-streptavidin conjugates. 1998 Bioconjugate Chemistry 9:168-175.*

Fong, et al. Thermoprecipitation of streptavidin via oligonucleotide-mediated self-assembly with Poly (N-isopropylacrylamide) 1999 Bioconjugate Chemistry 10:720-725.*

* cited by examiner

END GROUP ACTIVATED POLYMERS WITH OLIGONUCLEOTIDE LIGANDS

This application is a 371 of PCT/US02/03341, filed Feb. 04, 2002, and claims priority to provisional application 60/266,081 filed Feb. 02, 2001.

BACKGROUND OF THE INVENTION

1. Field of the Invention

The present invention relates to methods for modifying material surfaces to control cell response and for cell culture and analysis. More specifically, the present invention relates to methods for immobilizing a number of biomolecules in a defined ratio on a substrate for use in cell culture, medical devices and cell analysis.

2. Technical Background

Normal development and function in living organisms require interactions between cells and their environments. One way cells interact is through molecules that span the membrane of the cell called transmembrane proteins. When the portion of the transmembrane protein which is outside of the cell encounters specific molecules in the surrounding environment, the transmembrane protein undergoes structural and conformational changes which trigger biological reactions inside the cell.

Cells in vivo form complex multilayer structures which ultimately form tissues and organs. Tissue and organ formation, however, requires specific contacts between cells and their environments. Cells that require contact with their environment for proper development are referred to as "anchorage-dependent" because they will not grow properly, if at all, unless they are anchored to other cells, an extracellular matrix (ECM), or other surface.

An ECM is a complex and variable array of molecules secreted by cells, such as collagens, glycosaminoglycans, proteoglycans, and glycoproteins. Together these cellular products form the basal lamina, bone, and cartilage which give tissues and organs their shape and strength. In fact, contact between anchorage-dependent cells and the ECM in many instances plays a dramatic role in determining the cells' shape, position, metabolism, differentiation and growth.

Cell contact is also important in other biological functions, such as the activation of an immune response. The immune system is a complex network of cells that have the ability to recognize and rid the body of foreign substances, such as viruses, bacteria and parasites. One mechanism used by the immune system to rid itself of foreign substances is a humoral response. A humoral response involves activation of specific cells called B cell lymphocytes. B-cells are activated when transmembrane proteins on their surface bind to foreign substances called antigens. Specifically, binding of B-cells to antigens stimulates B cells to proliferate and differentiate into immunoglobulin or antibody producing plasma cells.

The antibodies produced by plasma cells travel throughout the body binding to the pathogen or foreign substance. Binding of antibodies to foreign substances activates several other immunological pathways, including the "complement" pathway. The complement pathway is designed to destroy the foreign substance and to initiate an inflammatory response in the organism.

While cell contact with other cells and the environment is important to the overall health and biological function of an organism, it creates unique problems in the biological sciences. Tissue or cell cultures comprise cells from a plant or animal which are grown outside the organism from which they originate. These cells are often grown, for example, in petri dishes under specific environmental conditions. Cell cultures are of great importance because they represent biological "factories" capable of producing large quantities of biological products such as growth factors, antibodies, and viruses. These products can then be isolated from the cell cultures and used for therapeutic purposes, for additional research, or for other uses.

Cell cultures are also a potential source of tissue which could be used for transplantation into an organism. For example, cell cultured skin cells may potentially be used in skin grafts to replace diseased or damaged skin. Cell cultures usually comprise cells from only one or a few tissues or organs. Consequently, cell cultures provide scientists with a system for studying the properties of individual cell types without the complications and risk of working with the entire organism. For example, the effects of pharmaceutical drugs on certain cell types could be tested on cell cultures prior to clinical trials in order to assess the drug's health risks.

Like most cells in vivo, cells grown in culture are either anchored to an ECM or another cell. Only cells of the circulatory system (e.g., lymphocytes and red blood cells) grow unattached and suspended in solution in vitro. Many anchorage-dependent cells can grow on glass or plastic surfaces, such as polystyrene. These cells, however, often lose their natural architecture and do not function normally. Cultured cells frequently lose the ability to differentiate and to respond to hormones. Accordingly, cells in culture do not precisely mimic a cell's biological functions in vivo and thus have limited potential.

For this reason, glass and plastic cell culture dishes are often coated width an ECM protein such as collagen, fibronectin, laminin and the like. These proteins bind to surfaces such as polystyrene through a process known as adsorption. Although ECM coated cell culture surfaces have led to improved culture conditions, they are far from ideal.

First, biomolecules, such as proteins, often become inactivated upon adsorption to hydrophobic surfaces. The biological activity of proteins is conferred by their unique structure and their ability to undergo conformational changes upon binding to a substrate or other physiological event. In one study, the structure of proteins was measured using a technique called microcalorimetry. Microcalorimetric studies demonstrated that proteins which are bound to hydrophobic surfaces loose essentially all their cooperatively folded structure compared to the same protein in solution. Because a protein's structure and its ability to undergo conformational changes strongly correlates with biological activity, these data suggest that most proteins that are adsorbed by a hydrophobic surface lose their in vivo biological activity.

Second, the conformation and orientation of immobilized proteins have important effects on the nature of their interaction with cells. D. J. Juliano, S. S. Saaedra and G. A. Truskey, Journal of Biomedical Materials Research 2-7 1103-1113 (1993). Both are influenced by the chemistry and physical properties of the underlying substrate as well as by the method of immobilization. K. Lewandowska, E. Pergament, N. Sukenik and L. A. Culp, The Journal of Biomedical Materials Research 21 1343-1363 (1992).

Third, like cells in vivo, cells in culture release molecules such as serum proteins and growth factors into the culture media. As discussed above, the secretion and concentration of these molecules in the culture media are needed for the proper biological function of neighboring cells. Under current cell culture conditions, the careful balance and concentration of secreted molecules are disrupted because secreted molecules are adsorbed by the cell culture surface. Thus, the communication and biological function of cells grown under current cell culture techniques does not mimic in vivo environment.

Finally, the surface concentration of ECM components is a factor in the regulation of cell behavior. The ability to control and vary surface biomolecule concentration depends on the method of immobilization and in some cases the physical nature of the base material. Simple ECM adsorption to cell culture substrates does not meet these requirements.

Moreover, a complex variety of biomolecules such as proteins, hormones, and the like are required for the normal growth and development of cells. In vivo these molecules are present in specific concentrations and ratios. If the ratio of the biomolecules is altered, the growth, metabolism, and function of the cell may be altered. The ability to coimmobilize two or more biomolecules in defined ratios on a single substrate would be useful to better mimic the in vivo environment. Methods that are currently used to immobilize biomolecules on material surfaces for in vitro cell growth, high throughput screening, biomolecule research and development, diagnostics, medical devices or bioreactors include direct adsorption and covalent coupling. These methods do not allow one to coimmobilize two or more biomolecules in defined ratios that can be readily varied on a single substrate.

In light of the foregoing, it would be a significant advancement in the art, to provide a system for growing cells in vitro that better mimics the in vivo environment of cells. It would be an additional advancement in the art to provide a method of coating tissue culture surfaces with biomolecules that does not destroy the biological activity of the biomolecule. It also would be an advancement in the art to provide a method of coating tissue culture surfaces that prevents nonspecific adsorption of proteins from the surrounding environment. It would be another advancement in the art, to provide a method for affixing two or more biomolecules to a surface in a defined ratio. It would be a further advancement in the art if the biomolecule coated surface could be used to adhere prokaryotic and eukaryotic cells, viruses, and molecules for the purpose of biological assay. It would be yet a further advancement in the art if the biomolecule coated material could be used to direct cell behavior.

BRIEF SUMMARY OF THE INVENTION

The method and apparatus of the present invention has been developed in response to the present state of the art, and in particular, in response to the problems and needs in the art that have not yet been fully solved by currently available methods and systems for attaching cells and biomolecules to surfaces. To overcome the deficiencies of the current methods and systems, the present invention presents a method and system whereby biomolecules can be conjugated to a surface in a defined ratio. This may be useful for cell culture and analysis, for controlling cell responses to medical devices, and for controlling cell behavior in tissue engineering applications.

The present invention relates to methods for coimmobilizing a number, N, of types of biomolecules in a defined ratio on a substrate. The substrate can be for example polymer particles, magnetic particles, petri dishes, multiwell plates, tea flasks, roller bottles, array chips, sample collection containers, assay tubes, fibers, membranes, scaffolds, medical devices and the like. The substrate can be contacted with a copolymer that has at least one hydrophobic segment combined with one or more hydrophilic segments that offer pendant groups for modification and attachment of proteins. PEO- and PPO-containing triblock or diblock copolymers are presently preferred, but many other copolymers may be used in accordance with the present invention. A variety of different PEO- and PPO-containing copolymers may be used with the present method. For instance, copolymers of polybutadiene and PEO, polyimide and PEO, polymethyl-methacrylate and PEO, polystyrene and PEO, polybutylene oxide and PEO, Poly-L-lysine and PEO, polydimethysiloxane and PEO, poly-(t-butyl methacrylate) and PEO, and hydrocarbon blocks with PEO may be used. One currently preferred copolymer that may be used is PLURONIC® F108 available from BASF Corporation. Similar to the PLURONIC® brand copolymers, many of these other copolymers have been shown to adsorb well onto hydrophobic materials and have been shown to form a nice layer of PEO at the surface that can inhibit nonspecific protein adsorption. In addition to PEO, other hydrophilic segments that may be useful are sepharose-type materials and other polysaccharides as well as polyurethane. The copolymer can be contacted with the surface for a time sufficient for the copolymer to be adsorbed to the substrate. See, for example, the disclosure of U.S. Pat. Nos. 6,284,503, 5,728,588, and 5,516,703, which are incorporated herein by reference.

The copolymer has an activated end group. The activated end group may be selected from a large number of groups, which allow an oligonucleotide to be conjugated to a polymer. For example, the activated end group may have a 2-pyridyl disulfide group. The activated end group can be conjugated with N types of oligonucletides to form copolymer-bound oligonucleotides. Each type of copolymer-bound oligonucleotide corresponds to one of the N types of biomolecules. In other words, N types of copolymer bound oligonucleotides are mixed in a predetermined ratio in order to achieve the defined ratio.

The biomolecules can be conjugated to complementary oligonucleotides to form biomolecule-bound oligonucleotides. Each type of biomolecule can be conjugated to an oligonucleotide that is complementary to the corresponding copolymer-bound oligonucleotide.

The biomolecule-bound oligonucleotides can be hybridized to the copolymer bound oligonucleotides. Such hybridization creates a substrate with a defined ratio of coimmobilized biomolecules. The steps of conjugating the end groups of the copolymers with the oligonucleotides, contacting the substrate with the oligonucleotide modified copolymers, and conjugating the complementary oligonucleotides with the biomolecules can be performed in any order.

A variety of biomolecules may be coimmobilized on the substrate with the disclosed method. Such biomolecules may include but are not limited to proteins, glycoproteins, peptides, growth factors, cytokines, attachment factors, extracellular matrix factors, antibodies, antibody fragments, differentiating factors, lectins, polysaccharides, receptors, receptor fragments, transmembrane proteins, fragments of transmembrane proteins and the like.

The method of the present invention may have alternative embodiments, which allow the performance of the steps of the method in any order. In one such embodiment, the method includes the steps of conjugating N types of first oligonucleotides to the copolymers; mixing N types of oligonucleotide modified copolymers in solution in a defined ratio; contacting a substrate with the oligonucleotide modified copolymer solution; conjugating N types of biomolecules to second oligonucleotides; and hybridizing the second oligonucleotides to the first oligonucleotides. As with other embodiments of the method of the present invention, the copolymer has an activated end group. The activated end group may contain a 2-pryidyl disulfide group or other group, which allows the copolymer to be conjugated to a first oligonucleotide. The substrate is contacted with the copolymer for sufficient time for the copolymer to be adsorbed to the surface of the substrate.

The present invention also relates to the preparation of a surface for the attachment, growth, control of cell behavior, or analysis of cells. A first oligonucleotide can be conjugated to the PEO-containing triblock or diblock copolymer. The copolymer may be, for example, PLURONIC® F108. The oligonucleotide modified copolymer may be adsorbed onto such surfaces. A second oligonucleotide can be conjugated to a biomolecule. The biomolecule can be selected from a variety of biomolecules that promote cellular attachment, that promote the growth of cells, that regulate the differentiation status of cells, or that are useful in the analysis of cells. The second oligonucleotide is generally complementary to the first oligonucleotide, such that the second oligonucleotide can be hybridized to the first oligonucleotide. The surface may also be prepared to include a number, N, of types of biomolecules in a defined ratio. This may be accomplished by conjugating the biomolecules to oligonucleotides that are hybridized to complementary oligonucleotides conjugated to PEO- and PPO-containing triblock or diblock copolymers. The biomolecules may be, for example, proteins, glycoproteins, peptides, growth factors, cytokines, attachment factors, extracellular matrix factors, antibodies, antibody fragments, differentiating factors, lectins, polysaccharides, receptors, receptor fragments, transmembrane proteins, fragments of transmembrane proteins and the like.

BRIEF DESCRIPTION OF THE DRAWINGS

The invention will be described and explained with additional specificity and detail through the use of the accompanying figures in which.

DETAILED DESCRIPTION OF THE INVENTION

The present invention relates to methods for coimmobilizing a number, N, of types of biomolecules in a defined ratio on a substrate. The substrate can be for example polymer particles, magnetic particles, petri dishes, multiwell plates, tea flasks, roller bottles, array chips, sample collection tubes, assay tubes, fibers, membranes, scaffolds, medical devices, medical implants, and the like. The substrate can be contacted with a copolymer that has at least one hydrophobic segment combined with one or more hydrophilic segments that offer pendant groups for modification and attachment of proteins. The copolymers are used as tethering moieties to link biomolecules the surface of the substrate. PEO- and PPO-containing triblock or diblock copolymers are presently preferred. One such copolymer that can be used with the method of the invention, is PLURONIC® F108, a triblock copolymer having the structure (polyethylene oxide)$_{129}$-(polypropylene oxide)$_{56}$-polyethylene oxide)$_{129}$. The substrate can be contacted with the surface for a time sufficient for the copolymer to be adsorbed to the substrate.

The terminal hydroxyl groups of the copolymer are activated to allow for binding of the copolymer to an oligonucleotide. As used herein, oligonucleotide includes polymers of Deoxyribonucleic Acids (DNA), Ribonucleic Acids (RNA), Peptidenucleic Acid (PNA), and polymers of nucleic acids containing modified or nonstandard bases. The end groups of a copolymer such as PLURONIC® F108 can be activated to incorporate a pyridyl disulfide moiety using the procedure of Li et al., *Bioconj. Chem.* 7:592-599 (1996). In this procedure, PLURONIC® F108 is first activated with p-nitrophenol chloroformate. P-nitrophenol activated F108 is then reacted with 2-(2-pyridyl dithio)ethylammonium chloride to produce a 2-pyridyl disulfide derivative of PLURONIC® F108. This activated PLURONIC® is then conjugated to an oligonucleotide sequence having a terminal thiol group through the pyridyl disulfide group on the PLURONIC®.

The proteins or other biomolecules of interest are attached to complementary oligonucleotide sequences. The oligonucleotide modified copolymer will bind to hydrophobic surfaces through its center polypropylene oxide block. Once the modified copolymer is bound to the surface, the biomolecule attached to a complementary oligonucleotide sequence can be added. The biomolecule is bound to the surface with high affinity as a result of base pairing between the oligonucleotide sequence attached to the copolymer and the complementary oligonucleotide sequence on the protein or other molecule of interest.

Using this approach, a copolymer such as PLURONIC® F108 can be modified with numerous different oligonucleotide sequences that have a high and specific binding affinity for only their complementary sequence. Similarly, proteins and other molecules can be modified with numerous different complementary DNA sequences. By mixing multiple types of OLIGO-modified copolymers in defined ratios in solution and using this solution to coat a surface, one can produce a surface that displays multiple different attachment chemistries where the relative amounts of each type of chemistry can be readily controlled and systematically varied.

Subsequently one can add biomolecules having complementary oligonucleotide sequences, and these will bind selectively to the immobilized complementary sequences. In this way, the relative amount of each type of protein that is coimmobilized on the surface can be tightly controlled. For practical purposes, the number of oligonucleotide pairs that can be employed is inexhaustible. Thus, there is no limit to the number of different factors that can be coimmobilized in selected ratios on a single surface.

A variety of biomolecules may be coimmobilized on the substrate with the disclosed method. Such biomolecules may include but are not limited to proteins, glycoproteins, peptides, growth factors, cytokines, attachment factors, extracellular matrix factors, antibodies, antibody fragments, differentiating factors, lectins, polysaccharides, receptors, receptor fragments, transmembrane proteins, fragments of transmembrane proteins, DNA, RNA, and the like.

Figure 3A:
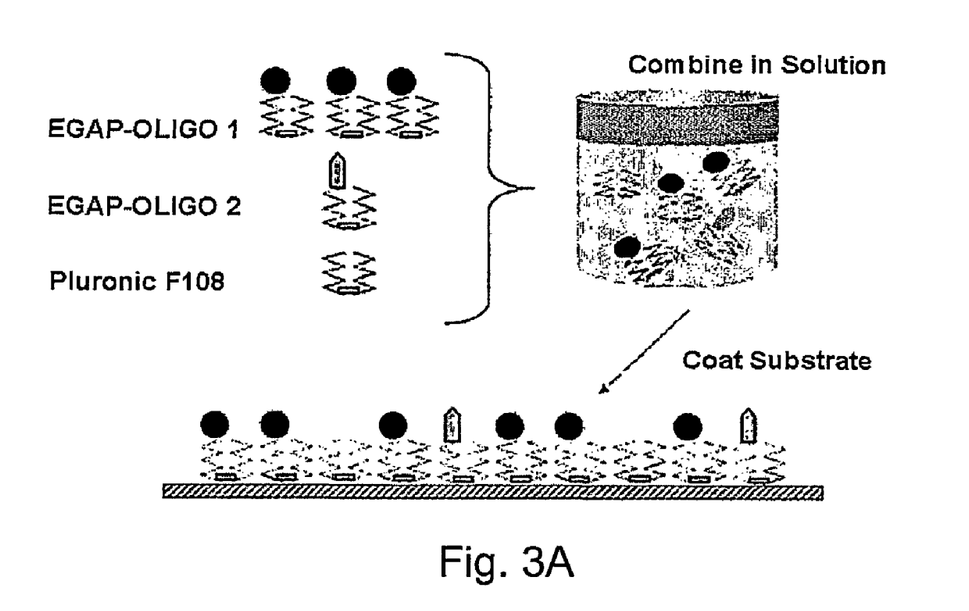
FIGS. 3A and 3B are schematic representations of the steps used to coimmobilize, in predetermined amounts, two different proteins using two different copolymer bound oligonucleotides and unmodified copolymer.
Figure 3B:
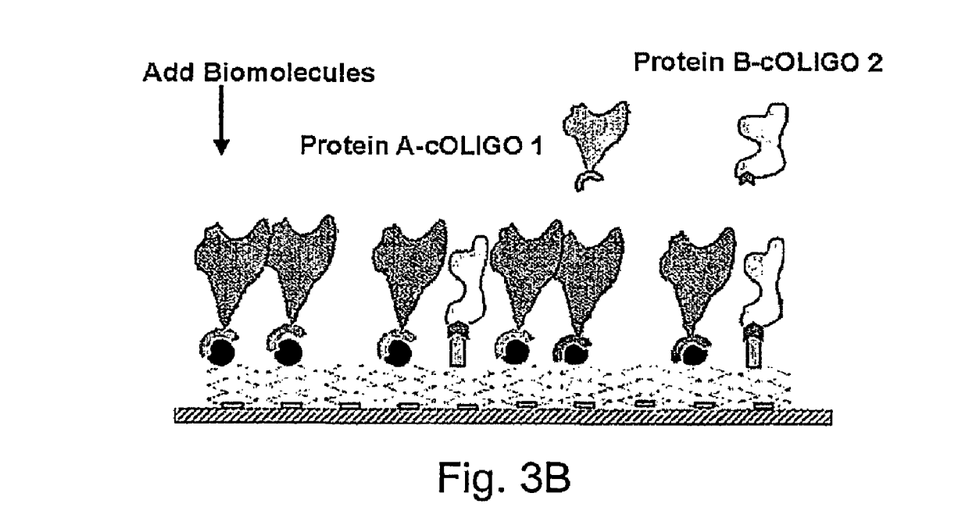

FIGS. 3A and 3B illustrate one possible embodiment within the scope of the present invention, which includes the steps of conjugating N types of first oligonucleotides to the copolymers; mixing N types of oligonucleotide modified copolymers in solution in a defined ratio; contacting a substrate with the oligonucleotide modified copolymer solution; conjugating N types of biomolecules to second oligonucleotides; and hybridizing the second oligonucleotides to the first oligonucleotides. The order of steps may be varied.

The present invention may be used to immobilize biomolecules on substrates for cell sorting. For example, numerous different types of substrates could be modified, including polymer particles, magnetic particles, petri dishes, multiwell plates, tea flasks, roller bottles, array chips, sample collection and assay tubes etc. The substrate is modified to display one or more types of biomolecules that are known to have a high and specific affinity for the cell type of interest using a copolymer bound oligonucleotide. The sample containing the cell type of interest is incubated with the modified substrate and the target cell binds to the immobilized biomolecules for which it possesses specific affinity. The substrate is washed to remove unwanted cells and proteins leaving only the target cell. The cells may then be grown for various applications, analyzed on the substrate or they can be harvested from the substrate by simply adding a reducing agent. The reducing agent will cleave the bonds between immobilized copolymer molecules and oligonucleotides and, in turn, will release the biomolecules and attached cells. This approach is useful for modifying multiwell plates or producing chips that display arrays of different cell types. For example, 96 well plates could be used to create a cell type array from a single tissue sample or patient sample and used in diagnostic testing.

The method of the present invention may be used to prepare surfaces with coimmobilized biomolecules. Such coated surfaces can be prepared with different domains for cell attachment or which are free from cells. Thus, a substrate may be prepared with domains that promote cell attachment and domains that inhibit cell attachment. For example, in one domain of the substrate a first copolymer-bound oligonucleotide may be adsorbed and in another domain of the substrate a second copolymer-bound oligonucleotide may be adsorbed. An oligonucleotide complementary the first copolymer-bound oligonucleotide may be conjugated to a biomolecule which promotes cell attachment and an oligonucleotide complementary to the second copolymer-bound oligonucleotide may be conjugated to a biomolecule which prohibits cell attachment. Thus when the complementary oligos and cells are added, a cell free domain is created.

The present invention may also be used to prepare patterned substrates for cell growth that have two or more types of domains in which each type of domain has a different biological activity. Each type of domain is created by adsorbing a copolymer-bound oligonucleotide or mixture of copolymer-bound oligonucleotides on the desired area(s) and subsequently adding biomolecules having complementary oligonucleotides. Such substrates will be useful for improved mimicking of tissue architecture on artificial substrates and scaffolding materials.

The present invention may be used to coat biomedical implants and devices to improve their interactions with cells and tissues. The coatings may be used to promote attachment and growth of specific cell types on implants or to regulate the behavior of cells that attach to implants. The coatings may be used to prevent adverse responses to implants by incorporating factors that inhibit response cascades, for example the coatings may be used to incorporate antithrombotic factors to prevent thrombus formation on cardiovascular devices. The coatings may be used to display therapeutic factors on temporary support materials such as sutures or bum would barriers that enhance wound healing.

The present invention may also provide substrates for in vitro drug development and toxicity testing. For example, small molecule drugs may be coimmobilized with biomolecules of interest in order to facilitate in vitro drug development and toxicity testing.

Containers for transfection of cells and subsequent detection of their recombinant protein expression products for evaluation of cellular transfection efficiencies and protein expression levels can be prepared by the present method. For example, a substrate may be modified to display one type of protein that will promote cell attachment to the substrate and a second type of protein that will capture the cellular expression product of interest. This is done using two different types of copolymer-bound oligonucleotides that are prepared as described herein. These type types of copolymer-bound oligonucleotides are referred to here as a and b. The protein that is used to promote cell attachment, referred to here as A, and the protein that is used to capture the recombinantly expressed protein, referred to here as B, are modified by attaching oligonucleotide sequences that are complementary to the oligonucleotide sequences on copolymer-bound oligonucleotide a and b, respectively. If the desired ratio of A:B is 1:3, one part copolymer-bound oligonucleotide a is combined with 3 parts copolymer-bound oligonucleotide b in water and the resulting solution is used to coat the transfection container. The different types of copolymer-bound oligonucleotides will adsorb in the same manner and to the same extent resulting in a surface ratio of a:b of 1:3. After coating, the container is washed and then incubated with proteins A and B. The proteins are bound to the immobilized copolymer-bound oligonucleotides through hybridization of their complementary oligonucleotide sequences and their resulting surface densities will reflect the surface ratios of copolymer-bound oligonucleotides a and b. The cells are seeded on the modified substrates and attach through protein A. The cells could be transfected either before or after they are seeded on the substrate. The cells are allowed adequate time for protein expression and are then lysed to release the recombinantly expressed protein. This protein is bound to the surface through protein B. The surface is washed to remove cellular debris and subsequently analyzed for the expressed protein.

The invention is also useful for producing containers for transfection of cells and subsequent detection of their recombinant protein expression products to determine activities of expressed proteins, stabilities of expressed proteins, and post-translational modifications of expressed proteins. Such containers would facilitate the discovery of mutations that produce proteins that are more robust in harsh environments or that display enhanced bioactivity relative to their native counter parts.

A substrate may be prepared as described above with two types of copolymer-bound oligonucleotides, type a and type b, adsorbed to its surface. The cells are seeded on the modified substrates and attach through protein A. The cells could be transfected either before or after they are seeded on the substrate. The cells are allowed adequate time for protein expression and are then lysed to release the recombinantly expressed protein. This protein is bound to the surface through protein B and the surface is washed to remove cellular debris. Here, B serves to either (1) bind the protein to allow for subsequent detection of activity, stability, or presence of posttranslational modifications by a secondary method (2) bind the expressed protein only if it possesses some requisite conformation or posttranslational modification, or (3) act as a substrate for the expressed protein that will produce a detectable product if cleaved. In the second case, the presence of the expressed protein on the surface could subsequently be detected by immunoassay.

The present invention also provides methods for evaluating the effects of extracellular biomolecules, drugs, or combinations of such on the efficiency of recombinant protein expression in transfected cells and for producing optimal environments for cell bioreactors. For example, substrates are prepared by the method of the invention where a factor or combination of factors, referred to as A, are immobilized on the surface to provide signals that are expected to influence the cell's ability to express the recombinant protein. Here the factor(s) could be extracellular matrix adhesion proteins, cytokines, growth factors, proteoglycans, structural proteins, cell adhesion molecules, antibodies, antigens, inhibitors, drugs, or any combination of such. In addition to these factors, one could coimmobilize on the surface a biomolecule, referred to as B that would bind the recombinantly expressed protein. The cells are seeded on the modified substrate and attach to the surface through A. The cells could be transfected either before or after they are seeded on the substrate. The cells are allowed adequate time for protein expression and are then lysed to release the recombinantly expressed protein. In the case where the surface is modified with protein B, the expressed protein is bound to the surface through B and the surface is washed to remove cellular debris. Here, B serves to bind the protein to allow for detection of activity, stability, or presence of posttranslational modifications. Alternatively, if the recombinant protein is secreted by the cells, a solution based assay could be used to detect the recombinantly expressed protein.

A substrate may be prepared by the method of the invention that allows for the monitoring of changes in cellular physiology as a result of cell transfection. Thus, a substrate can be prepared with a protein A which facilitates cellular binding and a protein B which binds cellular products other than the recombinant protein. This substrate would be useful for evaluating the safety and efficacy of a genetic therapy by monitoring the changes in the cellular physiology as a result of the transfection. In this example, protein A could be an extracellular matrix adhesion protein, cytokine, growth factor, proteoglycan, structural protein, cell adhesion molecule, antibody, drug or any combination of such. Cells are seeded on the substrate and incubated for a given time period during which the cells are influenced by protein A. The cells are then lysed and the protein of interest is bound to the substrate by protein B. The cell debris is washed away and the amount and/or properties of the immobilized protein of interest are assayed.

The method of coimmobilizing biomolecules on a substrate can be used to evaluate cellular products of cells that are not adhesion dependant. Such cells can be transfected and directed to secrete recombinant proteins. These cells are placed in containers that are modified, using the present invention, to display a protein that will serve as a tool to analyze a recombinantly expressed protein. This protein could be a substrate for a recombinantly expressed enzyme or kinase, a protein that is activated or inhibited by a recombinantly expressed protein, or an antibody. These containers will be useful for evaluating and comparing, between samples, protein expression levels, protein activities, posttranslational modifications, or changes in protein properties that result from mutation of the native gene.

The method of the invention may also be used to facilitate cell transfection by a virus. For example, a container for cell transfection can be modified to display two or more types of biomolecules. One of the biomolecules contains an adhesion sequence that will bind a virus that is used for cell transfection. The other biomolecule(s) contains an adhesion sequence for the cells to be transfected. Viruses are added to containers modified in this way and bind to the surface through the virus binding biomolecules. Cells are then added and bind to the cell binding molecules. This immobilizes the cells and viruses in close proximity to one another, and thereby, increases the probability of cell transfection.

The method of the present invention may also be used to prepare biomolecule arrays of proteins, peptides, DNA, RNA, small molecules or drugs. Such arrays may have numerous different types of proteins, peptides, DNA, or RNA immobilized on a single surface or chip in a micropattern. Such biomolecule arrays will facilitate high throughput sample processing in genomic, transcriptomic, and proteomic research as well as in diagnostics and drug development work where tissue samples or cultured cells can be screened to determine differential protein expression patterns and other changes in cell physiology such as receptor activation.

For example, copolymer-bound oligonucleotides are prepared and dissolved in aqueous solutions. Microdroplets of the solutions can be transferred to a chip to produce a binding array. The chip is washed and then exposed to a solution of unmodified copolymer-bound oligonucleotide, which coats areas around the copolymer-bound oligonucleotide spots and acts to prevent nonspecific adsorption. The chip is washed and then incubated with either proteins or peptides that have been modified to incorporate complementary oligonucleotide sequences or DNA or RNA molecules that contain at one end sequences complementary to those tethered to the surface through the copolymer. Each type of protein or DNA is bound to the spot having complementary copolymer-bound oligonucleotides. In this way, an array of biomolecules is produced on the chip surface. Such arrays are useful for genomic, transcriptomic and proteomic research. In the case of protein arrays, the proteins could be antibodies, antigens, enzymes, lectins, extracellular matrix molecules, growth factors, cytokines, receptors, ligands, cell adhesion molecules, activators or inhibitors. The chip substrate could be glass, hydrophobized glass, metal, hydrophobized metal, solid polymer, porous polymer, or glass or metal having a polymer film.

The present invention is useful for preparing surfaces that display protein complexes. In cells, many proteins bind together with other proteins to form complexes that function in signal transduction. Understanding what proteins interact with each other and how protein complexes perform signaling functions is important for understanding normal cell physiology and abnormal cell behaviors. Today, the functions of many proteins are unknown. One way that a researcher can gain insight into an unknown protein's function is to determine what other proteins or protein complexes it interacts with. Surfaces that display protein complexes would be useful for this purpose and can be prepared using the method of present invention. For this application it is important that the immobilized proteins are sufficiently mobile and close to one another to interact. The present invention is ideal for this because (1) the termini of copolymers such as F108's polyethylene oxide chains retain a high level of mobility when bound to a surface (Li et al., supra) and (2) copolymer-bound oligonucleotides such as F108-OLIGOs adsorb onto a surface at a sufficiently high density to allow for close packing of proteins coupled through complementary oligonucleotide tags. Substrates that have been modified to display protein complexes would be incubated with a protein of interest to determine whether it binds to a complex containing proteins B, C, and D or a complex containing proteins B, E and G, for example. Such substrates could also be used to determine what proteins or environmental factors are required for a signaling event, such as a phosphorylation, to occur within a given protein complex.

It will be understood that the method of the present invention can be used to create a near limitless variety of substrates with different types of biomolecules bound in varying ratios. These substrates can be used to prepare substrates used for the purposes as described above, or for a number of other purposes. Thus, biomolecules such as microtubule motor proteins with other biomolecules on microparticles can be immobilized on a substrate for use with microtransport and microseparation devices. The present invention will be useful for preparing microspheres that have biomolecules coimmobilized with an oligonucleotide sequence where the oligonucleotide sequence is unique to the particle type and serves as an identification tag or addressing tool. The method of the invention may also be used for the coimmobilization of enzymes for coupled enzyme assays.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope. All publications, patents, and patent applications cited in this application are hereby incorporated by reference.

EXAMPLES

The following examples are given to illustrate several embodiments which have been made within the scope of the present invention. It is to be understood that these examples are neither comprehensive nor exhaustive of the many types of embodiments which can be prepared in accordance with the present invention.

Example 1

Attachment of Oligonucleotides to PLURONIC® F108

Figure 1:
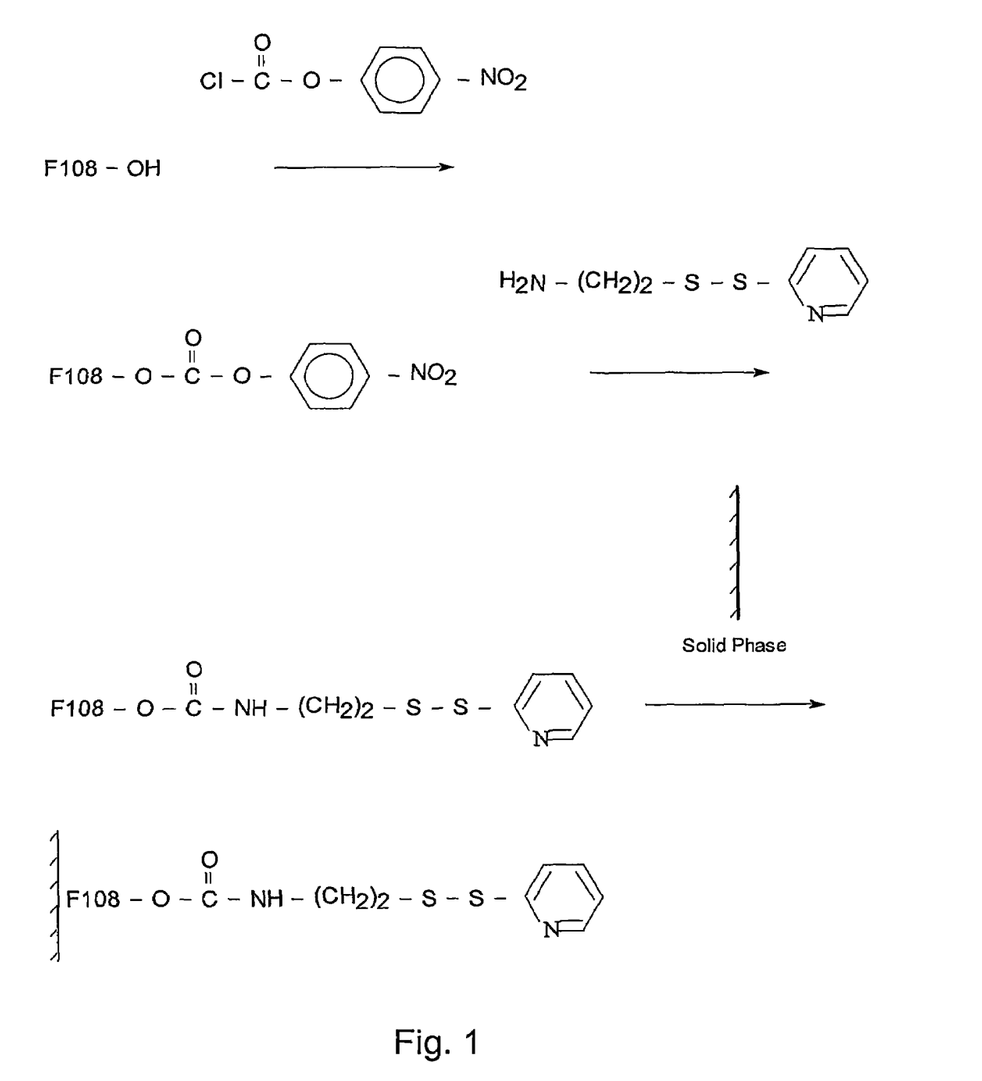
FIG. 1 is a schematic representation of the synthesis of a 2-pyridyl disulfide derivative of PLURONIC® F108 (EGAP).
Figure 2:
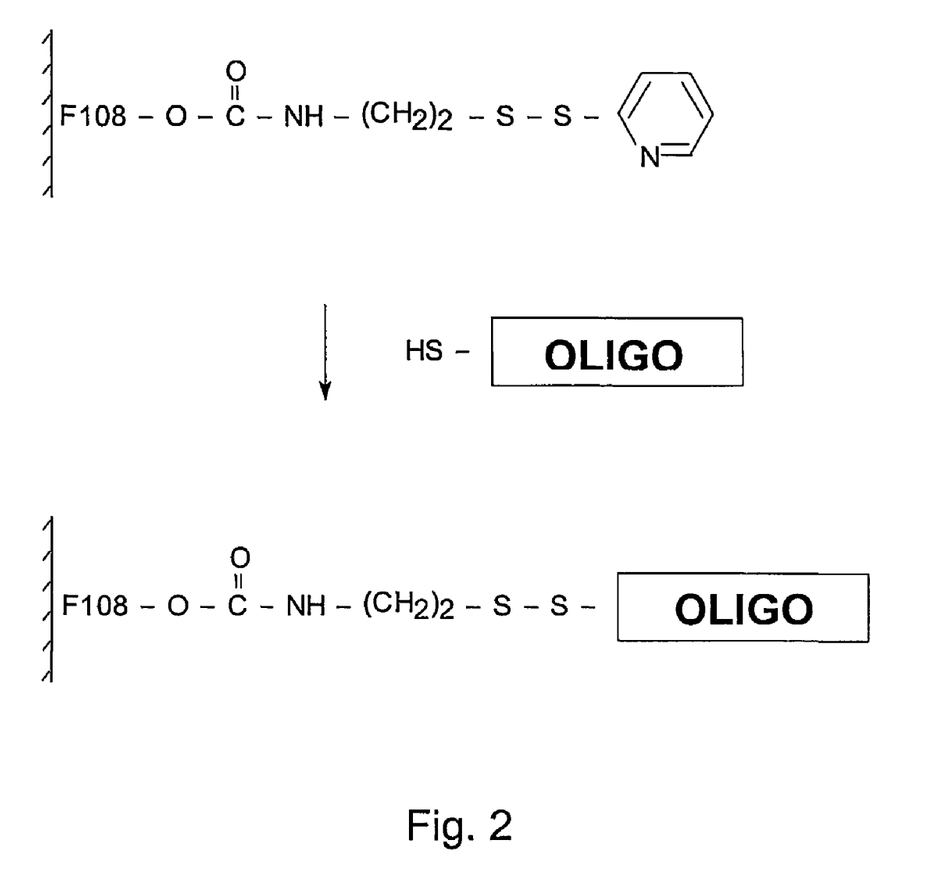
FIG. 2 is a schematic representation of the synthesis of representative copolymer-bound oligonucleotide that may be used with the method of the present invention.

A 2-pyridyl disulfide derivative of PLURONIC® F108 (EGAP) is synthesized according to the procedure of Li et al., supra (FIG. 1). F108 (6 g) is first activated with p-nitrophenyl chloroformate (0.5 g) in benzene (36 mL). The product is recovered by precipitation in ethyl ether and drying under vacuum. Mercaptoethylamine hydrochloride (3.4 g) is dissolved in a mixture of methanol (6 mL) and acetic acid (2.4 mL). This is reacted with 2, 2'-dithiopyridine (20 g) in methanol (90 mL) to obtain 2-(2-pyridyl dithio)ethylammonium chloride. The product is recovered by precipitation in ether and drying under vacuum. P-nitrophenyl chloroformate-activated F108 (3 g) is dissolved in methanol (9 mL) and is added to 2-(2-pyridyl dithio)ethylammonium chloride (1.8 g) dissolved in methanol (9 mL) containing TEA (1.24 mL) and allowed to react for 15-20 hours at room temperature. HCl is used to neutralize the TEA after completion of this reaction. The product, an F108 2-pyridyl disulfide derivative, is purified by dialysis and recovered by lyophilization. The degree of substitution is determined according to the method of Carlsson et al., *J. Biocheni.* 173:723-737 (1978). For this method, the UV absorbance at 343 nm of an exactly weighed portion of EGAP dissolved in phosphate buffered saline, pH 7.4 (PBS) is measured with respect to PBS. A 0.1 mL aliquot of 25 mM DTT is subsequently added to both the sample and reference cuvettes. The absorbance was again measured at 343 nm after 10 minutes of adding the DTT. To determine the concentration of released 2-thiopyridone, the difference in absorbance before and after the addition of DTT is taken and a molar extinction coefficient of 8060 $cm^{-1}M^{-1}$ is used. An oligonucleotide containing eight or more nucleotides and a terminal thiol group is dissolved in PBS. F108-PDS is dissolved in PBS and combined with the oligonucleotide solution (FIG. 2). The reaction mixture is placed on a shaker overnight at room temperature. The efficiency of the reaction is monitored by measuring the UV absorbance at 343 nm to determine the amount of pyridyl 2-thione released. The resulting oligonucleotide activated F108 (F108-OLIGO) is purified by dialysis and recovered by lyophilization.

Example 2

Modification of Substrates for Cell Attachment

The present invention may be used to modify artificial substrates for cell attachment. These substrates could be used to study how different biomolecules and specific combinations of biomolecules function to regulate cell growth and differentiation in embryogenesis and the development of both normal and diseased tissues. They could be used to grow cells in vitro for drug screening, toxicity testing and drug development. They could be used to grow cells in vitro for diagnostic or environmental monitoring devices. They could be used for bioreactors, tissue engineered devices for replacement of lost or damaged tissues, or implantable materials that function as structural support, delivery devices, in a reconstructive capacity, or in a regenerative capacity. It is well known that the differentiated status of cells is regulated by their microenvironments. Numerous biomolecules exist in in vivo cellular microenviromnents and both the types and concentrations of biomolecules present, as well as cell-cell interactions in these environments contribute to the regulation of cell behavior. In order to culture cells in vitro that maintain a desirable growth pattern or differentiation level, one must provide the cells with an appropriate microenvironment. For many cell types this will require a surface that displays more that one type of biomolecule where the surface density of each biomolecule is controlled. One can accomplish this using the present invention. As an example, one could coimmobilize four different biomolecules, referred to here as A, B, C, and D where A, B, C, and D could be extracellular matrix adhesion proteins, structural proteins, proteoglycans, cytokines, growth factors, lectins, receptors, ligands, cell adhesion molecules, antibodies, antigens, inhibitory factors or therapeutic agents. To do this, four different F108-OLIGOs, referred to here as a, b, c, and d, are prepared as described in Example 1. Biomolecules A, B, C, and D are modified to incorporate oligonucleotide sequences that are complementary to those of F108-OLIGOs a, b, c, and d, respectively. This can be done by first incorporating a sulfhydlyl reactive moiety on the biomolecule using a crosslinker such as N-[α-Maleimidoacetoxy]succinimide ester (AMAS) and subsequently, reacting with a thiolated oligonucleotide. To obtain final surface ratios of A:B:C:D of 1:2:3:4, one would combine one part a with two parts b, three parts c, and four parts d in solution. The total concentration of F108-OLIGOs that will be adsorbed onto the surface is then controlled by adding unmodified F108 to this solution. The F108-OLIGO solution is incubated with the material substrate of interest and the triblock copolymers adsorb to the material surface. The different types of F108-OLIGOs and unmodified F108 will adsorb in the same manner and to the same extent resulting in a surface ratios of a:b:c:d of 1:2:3:4. The substrate is typically a polystyrene surface but could be any sufficiently hydrophobic material including materials that have been modified to display hydrophobic surface properties. The substrate is washed and subsequently incubated with biomolecules A, B, C, and D. The oligonucleotide sequences attached to biomolecules A, B, C, and D will hybridize to their complementary sequences on the immobilized F108-OLIGOs a, b, c, and d, respectively. The substrate is washed and the resulting surface concentrations of biomolecules will reflect the surface concentrations of the different F108-OLIGOs immobilized. Cells are seeded on the modified substrate and allowed to respond to signals provided by the properties and concentrations of biomolecules, A, B, C, and D. The cells can be harvested from such surfaces by adding a mild reducing agent, such as glutathione or DTT. The reducing agent will cleave the bonds between immobilized F108 molecules and OLIGOs and in turn, will release the biomolecules and attached cells.

The invention claimed is:

1. A method of coimmobilizing a number, N, of different types of biomolecules on a substrate displaying hydrophobic surface properties, wherein N is a number greater than or equal to two, wherein the different types of biomolecules are coimmobilized on the substrate at a final surface ratio, and wherein a plurality of molecules of each of the different types of biomolecules are coimmobilized on the substrate, said method comprising the steps of:
   a. conjugating a first oligonucleotide to a triblock or diblock copolymer comprising polymer units selected from the group consisting of polybutadiene and PEO, polyimide and PEO, polymethylmethacrylate and PEO, polystyrene and PEO, polybutylene oxide and PEO, Poly-L-lysine and PEO, polydimethylsiloxane and PEO, and poly-(t-butyl methacrylate) and PEO having an activated end group to form a first copolymer-bound oligonucleotide, and repeating this conjugating step with N−1 additional oligonucleotides, each additional oligonucleotide bearing a different sequence from the first oligonucleotide and each other additional oligonucleotide, to form N different copolymer-bound oligonucleotides;
   b. combining the N different copolymer-bound oligonucleotides in solution to form a mixture of copolymer-bound oligonucleotides wherein each of the N different copolymer-bound oligonucleotides is selected to hybridize to one of N different complementary oligonucleotides, wherein the molecular quantity of one copolymer-bound oligonucleotide compared to the molecular quantity of N−1 other copolymer-bound oligonucleotide defines a ratio of copolymer-bound oligonucleotides in the mixture;
   c. contacting the substrate with the mixture of copolymer-bound oligonucleotides for a time sufficient for said copolymers to be adsorbed to the substrate such that the molecular quantity of said one copolymer-bound oligonucleotide adsorbed to the substrate compared to the molecular quantity of said N−1 other copolymer-bound oligonucleotide adsorbed to the substrate defines a ratio of copolymer-bound oligonucleotides adsorbed to the substrate that is substantially the same as the ratio of copolymer-bound oligonucleotides in the mixture;
   d. conjugating a biomolecule to a complementary oligonucleotide to form a biomolecule-bound complementary oligonucleotide, wherein the complementary oligonucleotide is selected to hybridize to one of the N copolymer-bound oligonucleotides, and repeating this conjugating step with N−1 different types of biomolecules and N−1 different complementary oligonucleotides to form N different types of biomolecule-bound complementary oligonucleotides; and
   e. hybridizing the biomolecule-bound complementary oligonucleotides to the copolymer-bound oligonucleotides to form N different types of biomolecules coimmobilized on the substrate wherein the molecular quantity of each different type of biomolecule compared to the molecular quantity of each other type of biomolecule defines a ratio of different types of biomolecules coimmobilized on the substrate, wherein the different types of biomolecules are coimmobilized on the substrate at the final surface ratio.

2. The method of claim 1, wherein one or more of the biomolecules is a protein or glycoprotein.

3. The method of claim 1, wherein one or more of the biomolecules is a peptide.

4. The method of claim 1, wherein one or more of the biomolecules is a growth factor.

5. The method of claim 1, wherein one or more of the biomolecules is an attachment factor.

6. The method of claim 1, wherein one or more of the biomolecules is an extracellular matrix factor.

7. The method of claim 1, wherein one or more of the biomolecules is an adhesion molecule.

8. The method of claim 1, wherein one or more of the biomolecules is a cytokine.

9. The method of claim 1, wherein one or more of the biomolecules is a lectin.

10. The method of claim 1, wherein the copolymer is a PEO- and PPO-containing triblock copolymer.

11. The method of claim 10, wherein the activated end group of the triblock copolymer comprises a 2-pyridyl disulfide.

12. The method of claim 1, wherein the biomolecules are antibodies.

13. The method of claim 1, wherein the substrate provides a surface for growth, directing cell behavior, or analysis of cells.

14. The method of claim 13, wherein the biomolecules are proteins or glycoproteins.

15. The method of claim 13, wherein one or more of the biomolecules is a peptide.

16. The method of claim 13, wherein the biomolecules are growth factors.

17. The method of claim 13, wherein the biomolecules are cellular attachment factors.

18. The method of claim 13, wherein one of more of the biomolecules is an attachment inhibition factor.

19. The method of claim 13, wherein the biomolecules are extracellular matrix factors.

20. The method of claim 13, wherein the copolymer is a PEO-and PPO-containing triblock copolymer.

21. The method of claim 20, wherein the activated end group of the triblock copolymer comprises a 2-pyridyl disulfide.

22. The method of claim 13, wherein the biomolecules are selected from antibodies, cell adhesion molecules, cytokines, polysaccharides, and lectins.

23. A method of coimmobilizing a number, N, of different types of biomolecules on a substrate displaying hydrophobic surface properties, wherein N is a number greater than or equal to two, wherein the different types of biomolecules are coimmobilized on the substrate at a final surface ratio, and wherein a plurality of molecules of each of the different types of biomolecules are coimmobilized on the substrate, said method comprising the steps of:
   a. conjugating a first oligonucleotide to a triblock or diblock copolymer comprising polymer units selected from the group consisting of polybutadiene and PEO, polyimide and PEO, polymethylmethacrylate and PEO, polystyrene and PEO, polybutylene oxide and PEO, Poly-L-lysine and PEO, polydimethylsiloxane and PEO, and poly-(t-butyl methacrylate) and PEO having an activated end group to form a first copolymer-bound oligonucleotide, and repeating this conjugating step with N−1 additional oligonucleotides, each additional oligonucleotide bearing a different sequence from the first oligonucleotide and each other additional oligonucleotide, to form N different copolymer-bound oligonucleotides;

b. conjugating a biomolecule to a complementary oligonucleotide to form a biomolecule-bound complementary oligonucleotide, wherein the complementary oligonucleotide is selected to hybridize to one of the N different copolymer-bound oligonucleotides, and repeating this conjugating step with N−1 different types of biomolecules and N−1 different complementary oligonucleotides to form N different types of biomolecule-bound complementary oligonucleotides;

c. hybridizing the N different copolymer-bound oligonucleotides with the N different types of biomolecule-bound complementary oligonucleotides to form N different types of biomolecule-copolymer constructs;

d. combining the N different types of biomolecule-copolymer constructs in solution to form a mixture of biomolecule-copolymer constructs such that the molecular quantity of each different type of biomolecule-copolymer construct compared to the molecular quantity of each other type of biomolecule-copolymer construct defines a ratio of different types of biomolecule-copolymer constructs in the mixture that is substantially the same as the final surface ratio; and e. contacting the substrate with the mixture of biomolecule-copolymer constructs for a time sufficient for said copolymers to be adsorbed to the substrate to form N different types of biomolecules coimmobilized on the substrate wherein the molecular quantity of each different type of biomolecule-copolymer construct adsorbed to the substrate compared to the molecular quantity of each other different type of biomolecule-copolymer construct adsorbed to the substrate defines a ratio of biomolecule-copolymer constructs adsorbed to the substrate, wherein the different types of biomolecules are coimmobilized on the substrate at the final surface ratio.

24. The method of claim 23, wherein one or more of the biomolecules is a protein or glycoprotein.

25. The method of claim 23, wherein one or more of the biomolecules is a peptide.

26. The method of claim 23, wherein one or more of the biomolecules is a growth factor.

27. The method of claim 23, wherein one or more of the biomolecules is an attachment factor.

28. The method of claim 23, wherein one or more of the biomolecules is an extracellular matrix factor.

29. The method of claim 23, wherein one or more of the biomolecules is an adhesion molecule.

30. The method of claim 23, wherein one or more of the biomolecules is a cytokine.

31. The method of claim 23, wherein one or more of the biomolecules is a lectin.

32. The method of claim 23, wherein the biomolecules are antibodies.

33. The method of claim 23, wherein the substrate provides a surface for growth, directing cell behavior, or analysis of cells.

34. The method of claim 23, wherein the copolymer is a PEO- and PPO-containing triblock copolymer.

35. The method of claim 34, wherein the activated end group of the triblock copolymer comprises a 2-pyridyl disulfide.

* * * * *

UNITED STATES PATENT AND TRADEMARK OFFICE
CERTIFICATE OF CORRECTION

PATENT NO. : 7,645,721 B2
APPLICATION NO. : 10/470296
DATED : January 12, 2010
INVENTOR(S) : Caldwell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 792 days.

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,645,721 B2 | |
| APPLICATION NO. | : 10/470296 | |
| DATED | : January 12, 2010 | |
| INVENTOR(S) | : Karin D. Caldwell et al. | |

It is certified that error appears in the above-identified patent and that said Letters Patent is hereby corrected as shown below:

IN THE SPECIFICATIONS:

In column 11, line 43, please delete "2-(2-pyridyl dithio)ethylamrn-" and replace it with --2-(2-pryidyl dithio)ethylam- --.

Signed and Sealed this
Seventeenth Day of May, 2011

David J. Kappos
*Director of the United States Patent and Trademark Office*